(12) United States Patent
Yamamoto

(10) Patent No.: US 7,060,142 B2
(45) Date of Patent: Jun. 13, 2006

(54) SEALING APPARATUS AND SEALING METHOD USING THE SEALING APPARATUS

(75) Inventor: Hiroki Yamamoto, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/059,448

(22) Filed: Feb. 17, 2005

(65) Prior Publication Data

US 2005/0145317 A1   Jul. 7, 2005

Related U.S. Application Data

(63) Continuation of application No. PCT/JP04/04525, filed on Mar. 30, 2004.

(30) Foreign Application Priority Data

Mar. 31, 2003   (JP) .............................. 2003-095069

(51) Int. Cl.
*B32B 37/00* (2006.01)

(52) U.S. Cl. .................. 156/73.1; 156/290; 156/308.4; 156/580.1; 156/580.2

(58) Field of Classification Search ............... 156/73.1, 156/290, 292, 308.2, 308.4, 555, 580.1, 580.2, 156/582, 583.1, 73.5, 73.6; 264/442, 443, 264/444; 425/174.2; 228/1.1, 110.1
See application file for complete search history.

(56) References Cited

U.S. PATENT DOCUMENTS

| 4,404,052 A | 9/1983 | Persson et al. |
|---|---|---|
| 4,614,078 A | 9/1986 | Kawabe |
| 4,713,132 A | 12/1987 | Abel et al. |
| 4,758,293 A | 7/1988 | Samida |
| 4,862,673 A * | 9/1989 | Francioni .................. 53/374.4 |
| 5,421,924 A * | 6/1995 | Ziegelhoffer et al. ...... 156/73.1 |
| 5,588,944 A | 12/1996 | Achelpohl et al. |
| 5,660,679 A | 8/1997 | Rajala et al. |
| 5,667,608 A | 9/1997 | Rajala et al. |
| 6,123,792 A | 9/2000 | Samida et al. |
| 6,309,487 B1 | 10/2001 | Herrin et al. |
| 6,368,437 B1 | 4/2002 | Ziegelhoffer et al. |
| 6,540,854 B1 | 4/2003 | Couillard et al. |
| 6,634,539 B1 | 10/2003 | Mlinar et al. |

FOREIGN PATENT DOCUMENTS

| JP | 02-43631 B2 | 10/1990 |
|---|---|---|
| JP | 04-13201 | 3/1992 |
| JP | 05-15551 A | 1/1993 |
| JP | 05-026005 | 2/1993 |
| JP | 06-027529 | 2/1994 |
| JP | 07-204223 | 8/1995 |
| JP | 08-132519 | 5/1996 |
| JP | 11-079109 | 3/1999 |
| JP | 2002-355270 | 12/2002 |
| WO | 96/23645 | 8/1996 |

* cited by examiner

*Primary Examiner*—James Sells
(74) *Attorney, Agent, or Firm*—Lowe Hauptman & Berner, LLP

(57) ABSTRACT

A sealing apparatus includes an anvil of a sealing abutment surface, which is driven to circulate with a constant peripheral velocity, and an ultrasonic horn of a sealing abutment surface, which is driven to reciprocate with varying velocities. Since the relative velocity of a soft workpiece moving along with the anvil against the sealing abutment surface of the ultrasonic horn can be made low, a sealing energy from the ultrasonic horn may be applied to the soft workpiece sufficiently long.

20 Claims, 6 Drawing Sheets

SEALING APPARATUS AND SEALING METHOD USING THE SEALING APPARATUS

This application is a continuation of International Application No. PCT/JP2004/004525 filed Mar. 30, 2004, which claims priority to Japanese Application No. 2003-95069 filed on Mar. 31, 2003, all of which are hereby incorporated by reference herein in their entirety.

BACKGROUND OF THE INVENTION

1. Field of the Invention

The present invention relates to a sealing apparatus for sealing (or welding) two or more sheets, such as thermoplastic films, thermoplastic nonwoven fabrics or a combination thereof, and a sealing method using the sealing apparatus, more particularly, relates to a sealing apparatus suitable for use in manufacturing an article having a seal, such as disposable diaper or sanitary napkin, and a sealing method using the sealing apparatus.

2. Description of the Related Art

Sealing apparatuses which can seal a stack of two or more sheets such as thermoplastic resin films or nonwoven fabrics comprising thermoplastic fibers by fusing the films or fibers are disclosed, for example, in Japanese Unexamined Patent Publication No. H05-15551 (Patent Publication 1) and Japanese Examined Patent Publication No. H02-43631 (Patent Publication 2). As disclosed in the Patent Publication 1, such a sealing apparatus may be installed in a process for manufacturing a disposable diaper or the like.

In order to seal a band-shaped soft workpiece such as the stack of resin films or nonwoven fabrics to have seals at a constant pitch in a feed direction of the workpiece or a seal continuously extending in the feed direction of the workpiece, it is necessary to firmly support the soft workpiece with a proper tension being given thereto. In a conventional sealing apparatus, accordingly, the workpiece is fed onto a periphery of a rotary drum so that as the rotary drum is driven to rotate, the workpiece moves in the direction of rotation, as in the Patent Publications 1 and 2. The workpiece thus fed and wound about the peripheral surface of the rotary drum may be firmly supported by the periphery of the rotary drum with a proper tension being given thereto.

Furthermore, the apparatus has an anvil disposed on the peripheral surface of the rotary drum and an ultrasonic horn for facing the anvil. The workpiece moving along with the peripheral surface of the rotary drum may be held between the anvil and the ultrasonic horn so as to be fused and sealed due to heat internally generated by ultrasonic vibration applied from the ultrasonic horn.

In such a conventional soft workpiece sealing apparatus, however, the ultrasonic horn is fixed in a position facing the peripheral surface of the rotary drum, as in the Patent Publications 1 and 2. Then, when the workpiece moving along with the peripheral surface of the rotary drum is held between the anvil and the ultrasonic horn, the ultrasonic vibration is applied from the ultrasonic horn to the workpiece that is sliding on the ultrasonic horn.

Accordingly, since the ultrasonic vibration from the ultrasonic horn cannot be applied sufficiently long to areas of the workpiece to be sealed, sealing failure tends to occur in the workpiece. Such sealing failure due to a decrease in vibrational energy applied to the workpiece may occur more frequently as the rotating velocity of the rotary drum is increased to let the workpiece move at a higher velocity for sealing, which results in an extremely high relative velocity of the workpiece and the anvil against the ultrasonic horn.

SUMMARY OF THE INVENTION

The present invention has been worked out in view of the shortcomings in the prior art set forth above. It is therefore an object of the present invention to provide a sealing apparatus wherein a relative velocity of a second holding member (e.g., ultrasonic horn) against a soft workpiece moving along with a first circulating holding member (e.g. anvil) is so decreased as to apply a sufficient sealing energy to the workpiece, thereby enabling high speed processing, and a sealing method using the sealing apparatus.

According to a first aspect of the present invention, there is provided a sealing apparatus comprising a first holding member of a first sealing abutment surface and a second holding member of a second sealing abutment surface and intended to hold a thermoplastic soft workpiece between the first and the second sealing abutment surfaces for sealing, the first holding member being disposed on a periphery of a rotor with the first sealing abutment surface directed radially outward, the second holding member being supported by a support with the second sealing abutment surface directed to face the first sealing abutment surface, wherein the apparatus further comprises rotational driving means for driving the rotor to rotate and reciprocating driving means for driving the support to put the second sealing abutment surface into reciprocating motion along a part of an orbital trajectory of the first sealing abutment surface, thereby enabling holding of the soft workpiece between the first and the second sealing abutment surfaces for sealing when the second holding member moves in the same direction as the first holding member.

In the sealing apparatus, since the second holding member is driven to reciprocate along a part of the orbital trajectory of the first sealing abutment surf ace of the first holding member, a relative velocity of the workpiece and the first folding member against the second holding member can be made low, so that a sealing energy can be applied to the workpiece sufficiently long with the first and the second holding members. Accordingly, sealing failure hardly occurs even when the rotor is driven to rotate with a high velocity for high speed processing.

When the number of first holding members disposed on the rotor is N, the reciprocating motion of the second holding member may be performed N cycles per rotation of the rotor.

The sealing apparatus may be constructed such that the first sealing abutment surface moves with a constant peripheral velocity as the rotor is driven to rotate with a constant angular velocity, whereas a peripheral velocity with which the second sealing abutment surface moves in the same direction as the first sealing abutment surface varies with time, so that the first and the second sealing abutment surfaces holding the soft workpiece therebetween for sealing move with a varying relative velocity. Since the relative velocity is extremely lower than the peripheral velocity of the first holding member, a sealing energy can be applied to the workpiece much longer than has been possible in the conventional sealing apparatuses. It should be noted that the relative velocity need not be zero, though the second sealing abutment surface may have a maximum velocity coinciding with the peripheral velocity of the first holding member to provide the moment when the relative velocity becomes zero.

In this case, preferably, two seal patterns separate from each other in a circumferential direction of the rotor are disposed on the first holding member, and the peripheral velocity of the second sealing abutment surface is adjusted in phase such that the relative velocity is reduced to a minimum when center of the second holding member is positioned midway between the two seal patterns. With the relative velocity reduced to a minimum at the midway position, relative velocities at the individual seal patterns may be equal when the workpiece is held between the first and the second holding members. Accordingly, since there may be eliminated any difference in sealing energy supply condition between the two seal patterns, sealing can be certainly performed with the two seal patterns, resulting in equal seal quality.

For example, the support may be allowed to perform an oscillating motion with a pivot thereof coinciding with or almost coinciding with a rotation center of the rotor, and the reciprocating driving means may be a crank mechanism for converting a uniform rotary motion into a reciprocating motion of the support. The crank mechanism may simplify the structure of the reciprocating driving means. In the present invention, it is also possible to adopt a cam as the reciprocating driving means and to control the reciprocating speed of the support by means of a cam profile, but since such a cam is expensive to process, it is desirable to construct the apparatus inexpensively with the crank mechanism.

In the sealing apparatus, a rotary shaft of the rotor may be movable toward the second holding member, and the sealing apparatus may further comprise pressure setting means for setting a holding pressure to be applied to the soft workpiece between the first and the second sealing abutment surfaces with the rotor pressed against the second holding member. With the pressure setting means, the holding pressure can be maintained properly.

In this case, preferably, the holding pressure to be set by the pressure setting means is so adjustable as to vary in accordance with a rotational velocity of the rotor. In the sealing apparatus of the present invention, since the relative velocity can be made low, a sealing energy may be applied to the workpiece sufficiently long with the first and the second holding members. However, if the rotational velocity of the rotor is significantly increased, the sealing energy will not be properly applied to the workpiece after all. In this case, increasing the holding pressure may result in certain formation of seals in the workpiece.

According to a second aspect of the present invention, there is provided a sealing method comprising holding a thermoplastic soft workpiece between a first holding member of a first sealing abutment surface and a second holding member of a second sealing abutment surface for sealing, wherein the first holding member is driven to circulate with the first sealing abutment surface directed outward in a direction normal to an orbital trajectory thereof, the soft workpiece is fed onto the first holding member so as to move along with the first sealing abutment surface, and the second holding member is driven to reciprocate along a part of the orbital trajectory with the second sealing abutment surface directed to face the first sealing abutment surface, wherein the first sealing abutment surface moves with a constant peripheral velocity, whereas a peripheral velocity with which the second sealing abutment surface moves in the same direction as the first sealing abutment surface varies with time, so that the first and the second sealing abutment surfaces holding the soft workpiece therebetween for sealing move with a varying relative velocity.

Also in the sealing method, it is preferred that two seal patterns separate from each other in a direction of circulation thereof are disposed on the first holding member, and the peripheral velocity of the second sealing abutment surface is adjusted in phase such that the relative velocity is reduced to a minimum when center of the second holding member is positioned midway between the two seal patterns.

The second holding member may be driven to reciprocate with a crank mechanism for converting a uniform rotary motion into a reciprocating motion.

When the number of first holding members circulating at a constant pitch is N, the reciprocating motion of the second holding member may be performed N cycles per circulation of each first holding member.

In the present invention, the soft workpiece may comprise liquid absorbent bodies arranged at an interval in a feed direction thereof and fusion-bondable sheets supporting the liquid absorbent bodies. A stack of the sheets may be held between the first and the second sealing abutment surfaces for sealing, at a position between adjacent liquid absorbent bodies.

The sealing apparatus and the sealing method are suitable for use in manufacturing an absorbent article, such as a disposable diaper or a sanitary napkin. Alternatively, the stack of the sheets, such as resin films or nonwoven fabrics, may be sealed prior to the manufacturing process of an absorbent article, such as a disposable diaper or a sanitary napkin.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
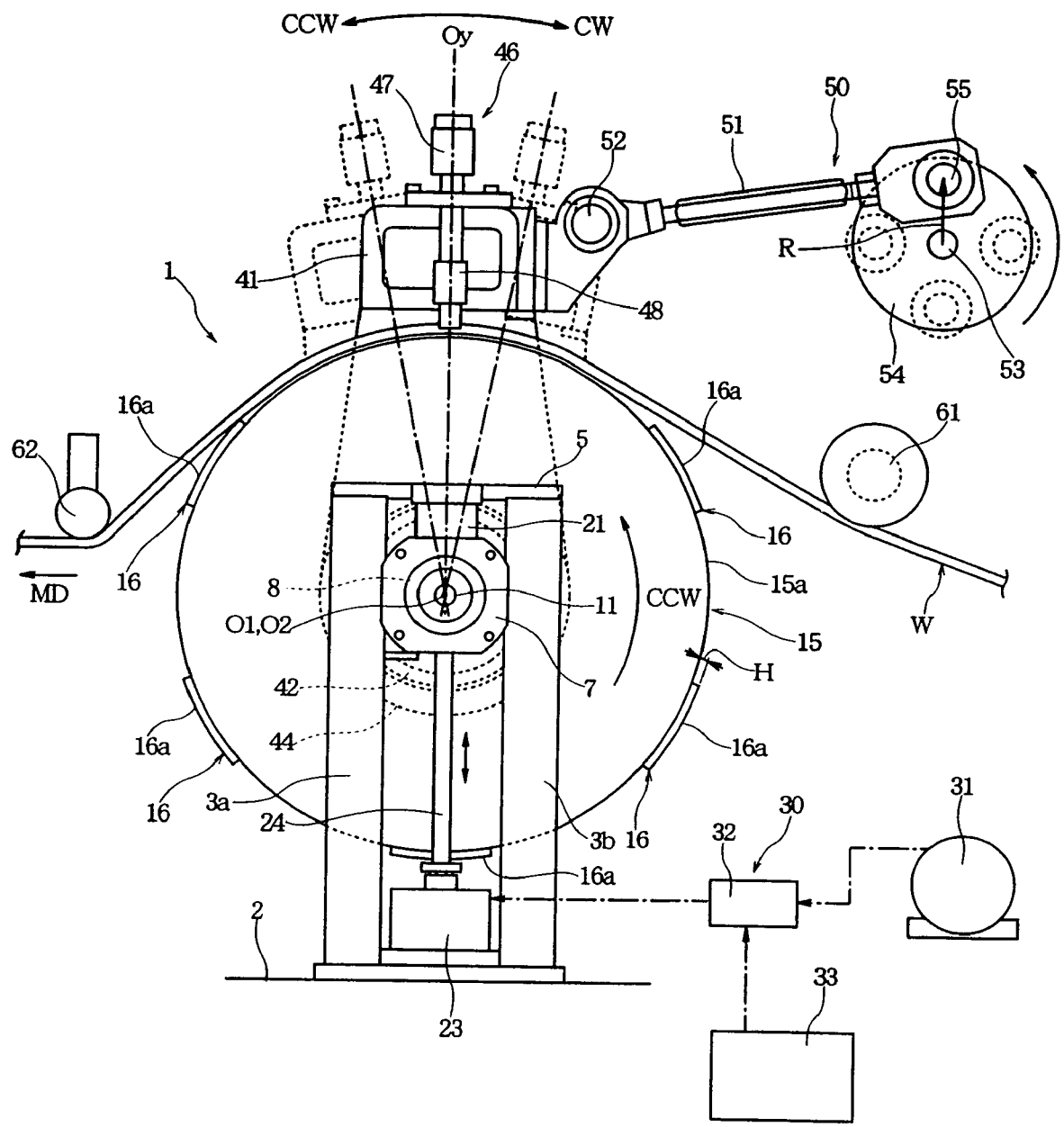
FIG. 1 is a front view of a sealing apparatus according to one embodiment of the present invention.
Figure 2:
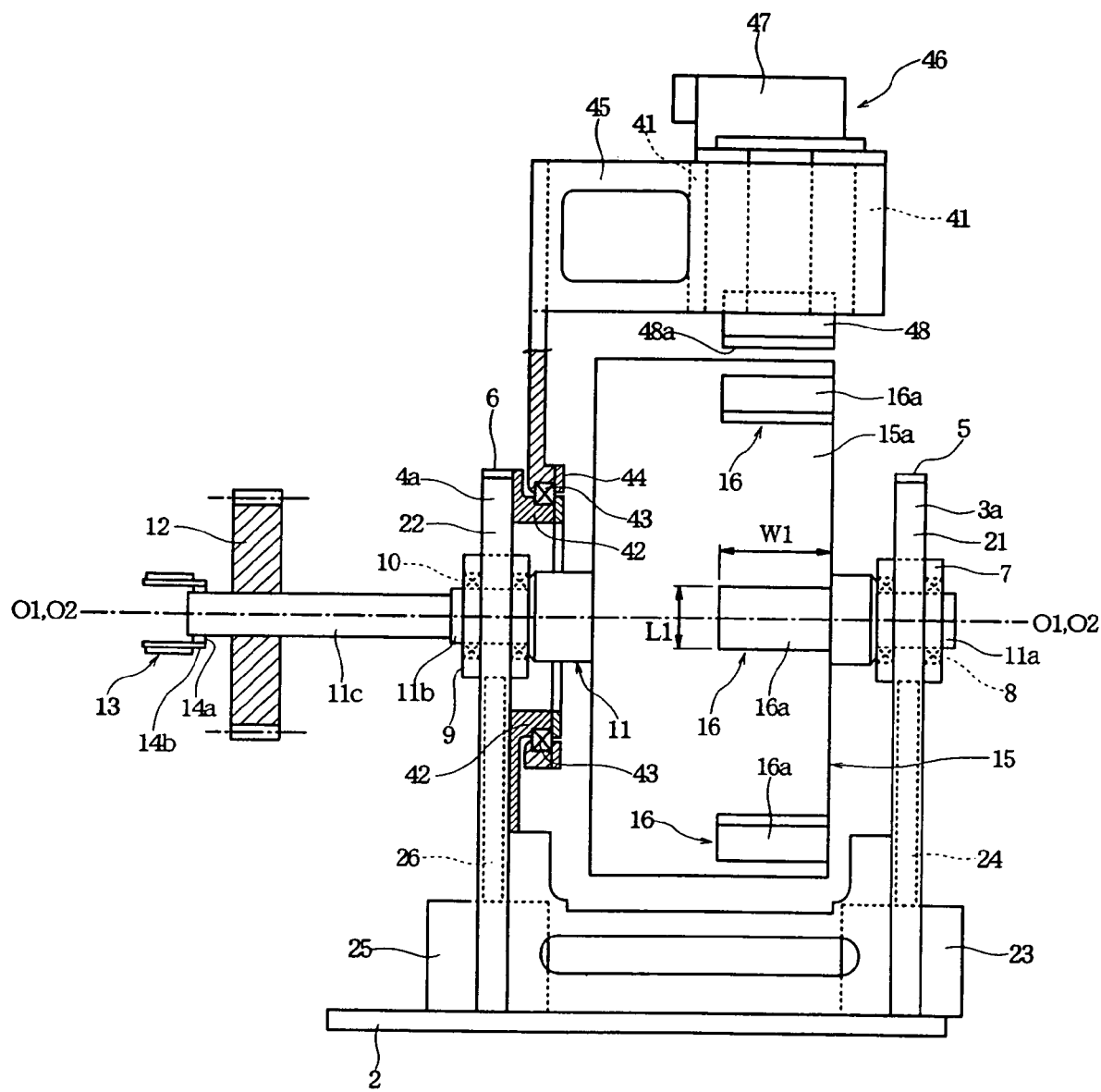
FIG. 2 is a left side view of the sealing apparatus.
Figure 3:
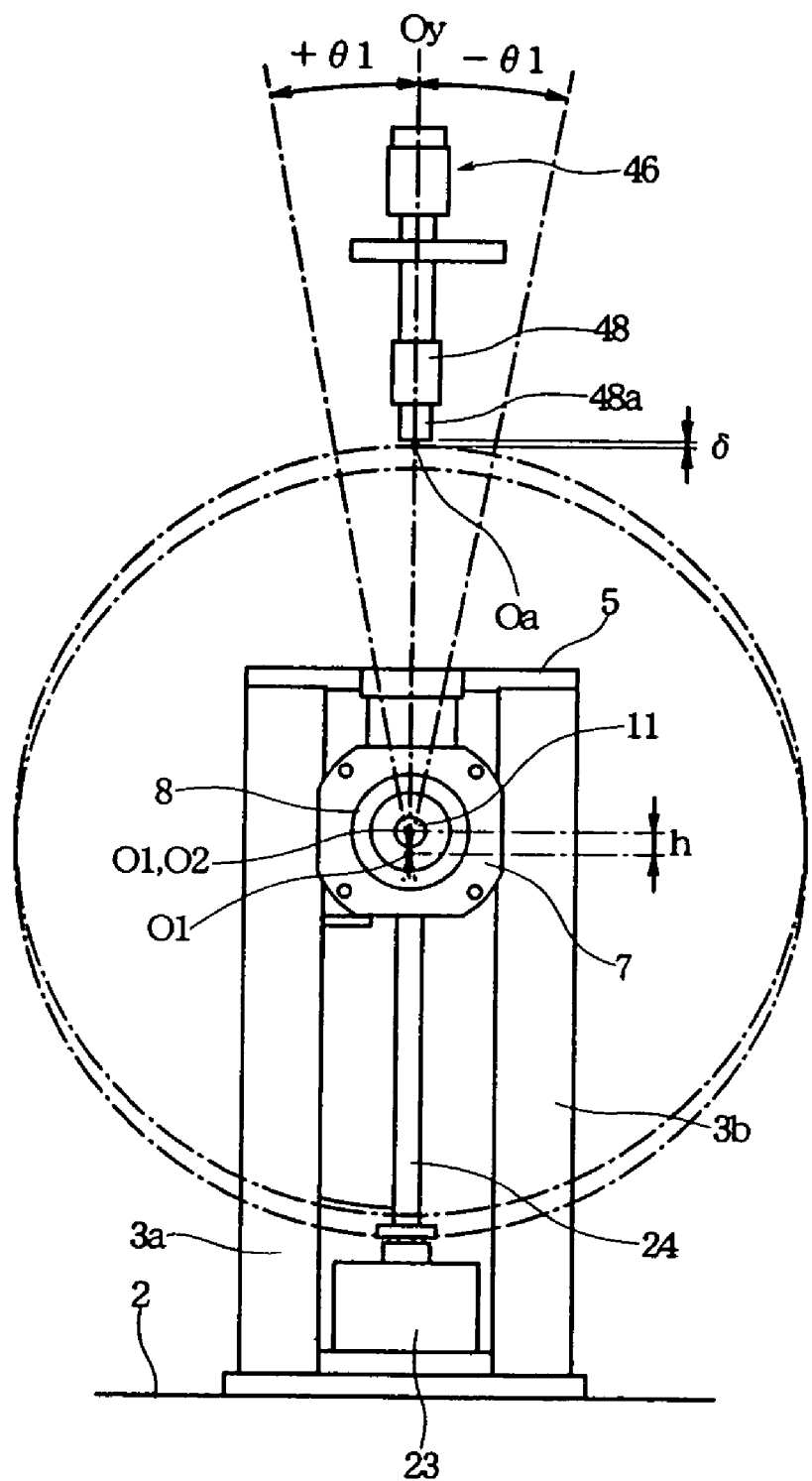
FIG. 3 is an explanatory diagram illustrating operation of the sealing apparatus.
Figure 4:
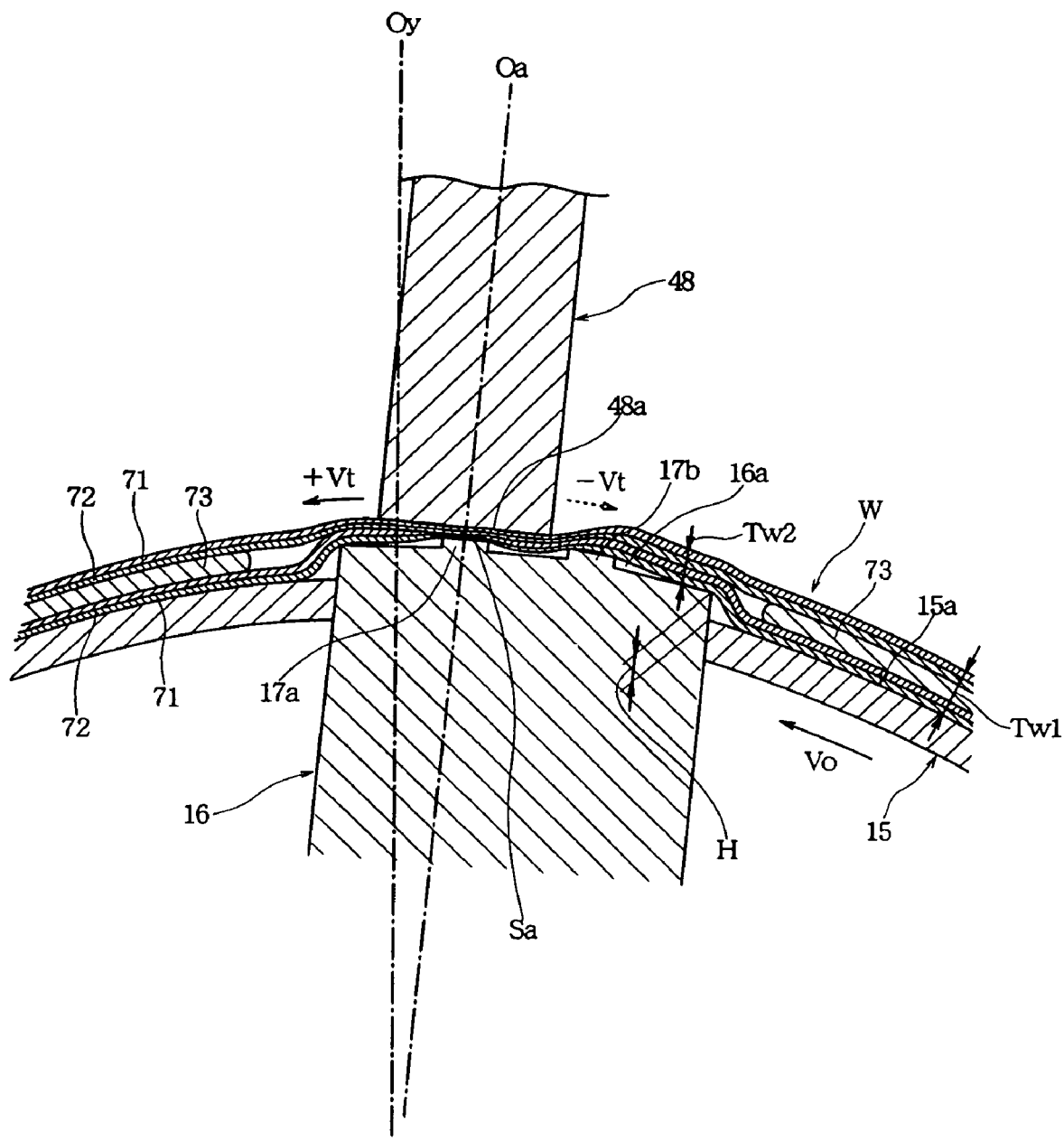
FIG. 4 is an enlarged sectional view showing one example of sealing operation.
Figure 5:
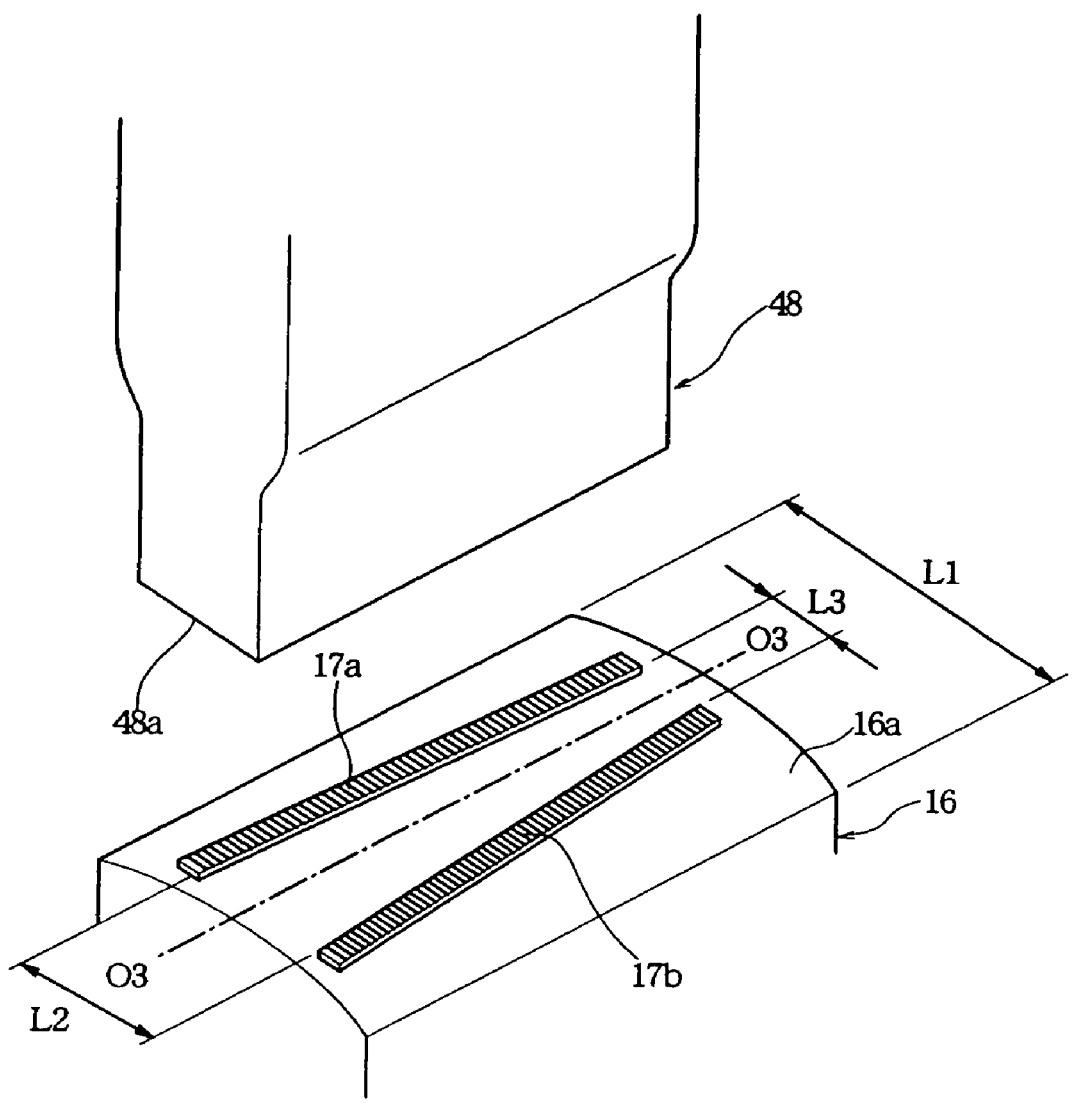
FIG. 5 is a perspective view showing a state where an anvil as first holding member and an ultrasonic horn as second holding member are opposed to each other.
Figure 6A:
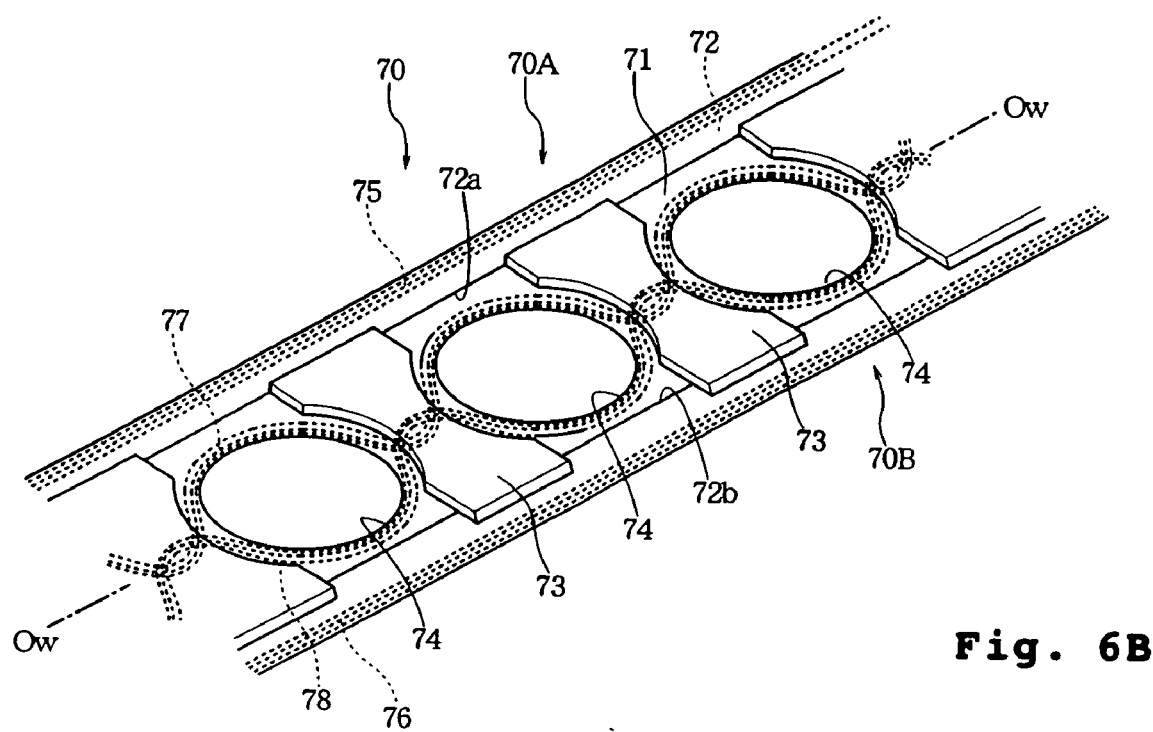
FIGS. 6A and 6B are perspective views showing one example of a soft workpiece.
Figure 6B:
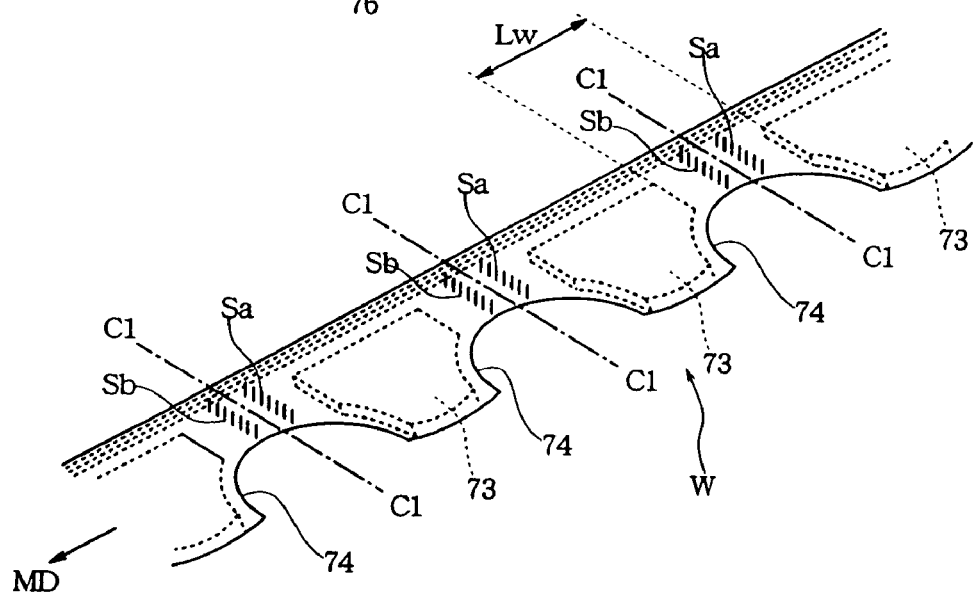

FIG. 1 is a front view of a sealing apparatus according to one embodiment of the present invention; FIG. 2 is a left side view of the sealing apparatus; FIG. 3 is an explanatory diagram illustrating operation of the sealing apparatus; FIG. 4 is an enlarged sectional view showing one example of sealing operation; FIG. 5 is a perspective view showing a state where an anvil as first holding member and an ultrasonic horn as second holding member are opposed to each other; and FIGS. 6A and 6B are perspective views showing one example of a soft workpiece.

In a sealing apparatus 1 shown in FIGS. 1 and 2, O1 represents a rotation center of a rotor, and Oy represents a vertical reference line vertically passing the rotation center O1. The side shown in FIG. 1, i.e., the right side shown in FIG. 2 is a front side of the sealing apparatus 1, while the left side shown in FIG. 2 is a rear side of the sealing apparatus 1.

The sealing apparatus 1 has a fixed table 2 as a fixed portion placed on a floor. In the front side of the sealing apparatus 1, there are provided front support frames 3a, 3b which extend vertically upward with their lower ends fixed to the fixed table 2. The front support frames 3a, 3b are an equal distance apart from the rotation center O1 horizontally to extend parallel with each other.

In the rear side of the sealing apparatus 1, there are also provided rear support frames 4a, 4b identical to the front support frames 3a, 3b. One rear support frame 4a appears in FIG. 2, but the other rear support frame 4b is hidden behind the rear support frame 4a in FIG. 2 and behind the front support frame 3b in FIG. 1. Also with their lower ends fixed to the fixed table 2, the rear support frames 4a, 4b extend upward parallel with each other.

As shown in FIG. 1, the upper ends of the front support frames 3a, 3b are connected to each other through a front support connecting plate 5, and the upper ends of the rear support frames 4a, 4b are likewise connected to each other through a rear support connecting plate 6.

Between the front support frames 3a, 3b, there is provided a front bearing holder 7 holding a bearing 8. Also between the rear support frames 4a, 4b, there is provided a rear bearing holder 9 holding a bearing 10.

A front portion 11a of a rotary shaft 11 is rotatably supported by the bearing 8, while an intermediate portion 11b of the rotary shaft 11 is rotatably supported by the bearing 10. The rotation center O1 coincides with a shaft axis of the rotary shaft 11.

Between the front support frames 3a, 3b and the rear support frames 4a, 4b, there is provided a rotor 15 which is fixed to the rotary shaft 11. The rotor 15 has a peripheral surface 15a that is a cylindrical surface with a given radius about the rotation center O1.

On the peripheral surface 15a of the rotor 15, there are disposed anvils 16 functioning as first holding member. The anvils 16 are at a constant pitch circumferentially on the peripheral surface 15a. In the present embodiment, the rotor 15 has six anvils 16 arranged at an angle of 60 degrees with respect to the rotation center O1.

The six anvils 16 are all of the same structure and size. As shown in FIG. 2, the anvils 16 have a dimension W1 in a direction parallel to the rotation center O1 and a dimension L1 circumferentially. Here, the each individual anvil 16 has a sealing abutment surface 16a (or first sealing abutment surface), which is directed outward in a direction normal to the peripheral surface 15a of the rotor 15 and at a distance H away from the peripheral surface 15a of the rotor 15 (see FIG. 1). It should be noted that the individual sealing abutment surfaces 16a of the anvils 16 coincide with the cylindrical surface of a given radius about the rotation center O1.

As shown in FIGS. 4 and 5, the sealing abutment surface 16a of the anvil 16 has two seal patterns 17a, 17b. These seal patterns 17a, 17b are formed to project from the sealing abutment surface 16a in the normal direction. In FIG. 5, O3 represents a centerline which bisects the sealing abutment surface 16a circumferentially. The seal patterns 17a, 17b are symmetrical about the centerline O3, so that a distance between one seal pattern 17a and the centerline O3 is equal to that between the other seal pattern 17b and the centerline O3.

However, the seal patterns 17a, 17b are separated from each other circumferentially with a maximum distance L2 on the front side and with a minimum distance L3 on the rear side, so that the individual seal patterns 17a, 17b are inclined to the centerline O3.

The seal patterns 17a, 17b are formed in surfaces of strip-shaped raised portions of a constant width, wherein projections and recesses alternate with each other in a longitudinal direction of each pattern. Accordingly, these projection/recess patterns may be transferred to a workpiece.

As shown in FIG. 2, the rotary shaft 11 has a rear portion 11c further extending rearward from the rear bearing holder 9, and a toothed pulley 12 is fixed on the rear portion 11c. Power from a motor (not shown) is transmitted to the toothed pulley 12 through a toothed belt (not shown), whereby the rotor 15 is driven to rotate with a constant angular velocity in a counterclockwise (CCW) direction of FIG. 1.

The each individual anvil 16 has a built-in cartridge heater for heating the anvil 16. The anvil 16 also has a temperature sensor for measuring a temperature of the anvil 16 heated by the cartridge heater. The anvil 16 may be maintained at a set temperature by controlling the cartridge heater based on a measured temperature.

The rear portion 11c of the rotary shaft 11 has feeding control means 13, as shown in FIG. 2. A conductive slip ring 14a is provided around the periphery of the rear portion 11c of the rotary shaft 11, and a slider 14b for sliding on the slip ring 14a is provided on a fixed side. The cartridge heater and the temperature sensor are electrically connected to the slip ring 14a, and the feeding control means 13 is electrically connected to slider 14b. Accordingly, when the rotor 15 is rotating, power is supplied from the feeding control means 13 to the cartridge heater through the slider 14b and the slip ring 14a, while a temperature measurement signal from the temperature sensor is applied to the feeding control means 13.

The front bearing holder 7 is supported so as to be vertically movable between the front support frames 3a, 3b, and the rear bearing holder 9 is also supported so as to be vertically movable between the rear support frames 4a, 4b. Beneath the front support connecting plate 5, as shown in FIGS. 1 and 2, there is provided a stopper 21. Likewise, a stopper 22 is provided beneath the rear support connecting plate 6.

The fixed table 2 is provided at its front side with a fluid cylinder (air cylinder) 23 as pressure setting means, wherein the fluid cylinder 23 has a reciprocating rod 24 whose upper end is connected to the front bearing holder 7. Likewise, the fixed table 2 is provided at its rear side with a fluid cylinder (air cylinder) 25 as pressure setting means, wherein the fluid cylinder 25 has a reciprocating rod 26 whose upper end is connected to the rear bearing holder 9.

The height position and inclination of the rotation center O1 of the rotary shaft 11 may be set with the front bearing holder 7 being pressed against the stopper 21 by the fluid cylinder 23 and the rear bearing holder 9 being pressed against the stopper 22 by the fluid cylinder 25. Here, the stoppers 21, 22 may be adjusted in vertical position independently from each other. Accordingly, fine adjustment of the individual stoppers 21, 22 in height position leads to fine adjustment of the rotation center O1 in height position and inclination.

In the present embodiment, a holding pressure to be applied to a workpiece during sealing operation can be set by a fluid pressure inside the fluid cylinders 23, 25. Additionally, the holding pressure during sealing operation may be adjusted when the rotational velocity of the rotor 15 changes. To this end, the sealing apparatus 1 includes pressure setting means 30 for setting the holding pressure by adjusting the fluid pressure inside the fluid cylinders 23, 25. The pressure setting means 30 comprises a fluid pump 31, an adjusting valve 32 for adjusting a fluid pressure from the fluid pump 31 to the fluid cylinders 23, 25, and a controller 33 for controlling the adjusting valve 32.

The controller 33 functions not only to adjust the adjusting valve 32 based on an operational input by an operator but also to automatically adjust the adjusting valve 32 in accordance with the rotational velocity of the rotor 15.

As shown in FIG. 2, a support 41 is rockably supported by the rear support frames 4a, 4b. A fixed ring 42 is fixed to the rear support frames 4a, 4b, and an inner ring of a ring-shaped roller bearing 43 is fixed to the fixed ring 42. On the other hand, a movable ring 44 is fixed to a base portion of the support 41, and an outer ring of the roller bearing 43 is fixed to the movable ring 44.

With the roller bearing 43, the support 41 is pivotally supported. A rotation center of the outer ring of the roller bearing 43 is a pivot O2 of the support 41. As understood from the structure shown in FIG. 2, the rotation center O1 of the rotor 15 and the pivot O2 of the support 41 are set independently from each other. Since the ring-shaped roller bearing 43 is fixed to the rear support frames 4a, 4b, the pivot O2 is immovable; but the rotation center O1 is adjustable in vertical position by adjusting the height positions of the stoppers 21, 22, as set forth above. Here, the rotation center O1 is positioned such that the pivot O2 coincides with the rotation center O1 or almost coincides with the rotation center O1.

A bracket 45 is fixed to an upper portion of the support 41, and a second holding member 46 is mounted on the bracket 45. This second holding member 46 comprises an ultrasonic vibration generator 47 composed of vibrator, amplifier and so on and an ultrasonic horn 48 to which the ultrasonic vibration is to be applied.

As shown in FIGS. 4 and 5, the ultrasonic horn 48 has a sealing abutment surface 48a (or second sealing abutment surface), which is directed to face the peripheral surface 15a of the rotor 15 and the sealing abutment surfaces 16a of the anvils 16. The sealing abutment surface 48a of the ultrasonic horn 48 is as large as can cover at least one of the seal patterns 17a, 17b of the anvil 16 and is substantially parallel to a plane tangent to the peripheral surface 15a of the rotor 15.

The second holding member 46 is adjustable in fixing position against the bracket 45, so that a clearance δ between the sealing abutment surface 16a of the anvil 16 and the sealing abutment surface 48a of the ultrasonic horn 48 (see FIG. 3) is adjustable. In the present embodiment, with the front bearing holder 7 being pressed against the stopper 21 and the rear bearing holder 9 being pressed against the stopper 22, the height position and inclination of the rotation center O1 may be finely adjusted by fine adjustment of the individual stoppers 21, 22 in height position, as set forth above. In addition to the inclination adjustment, however, the mounting angle of the second holding member 46 against the bracket 45 may be changed to adjust the angle between the two sealing abutment surfaces 16a, 48a.

As shown in FIG. 1, reciprocating driving means 50 is provided between a fixed plate (not shown) extending from the fixed table 2 and the support 41.

The reciprocating driving means 50 has a connecting rod 51 whose front end is pivotally connected to the support 41 through a connecting shaft 52. A shaft 53 is rotatably supported by the fixed plate, and a drive rotor 54 is fixed to the shaft 53. At its rear end, the connecting rod 51 is pivotally supported on the drive rotor 54 through a connecting shaft 55.

The reciprocating driving means 50 is a crank mechanism for converting a rotary motion of the drive rotor 54 into a reciprocating motion of the support 41. A toothed pulley is fixed on the shaft 53 of the drive rotor 54 so that a rotating power may be transmitted to the toothed pulley through a toothed belt. The drive rotor 54 and the rotor 15 are driven to rotate in synchronization with each other. For instance, power may be applied from a common motor to the drive rotor 54 and the rotor 15 after speed reduction. Alternatively, a motor for driving the rotor 15 may be provided separately from a motor for driving the drive rotor 54 and one motor be controlled based on detection signal of rotational velocity of the other rotor.

As a result, the drive rotor 54 and the rotor 15 are driven in synchronization with each other to provide a constant ratio between rotational velocities. They are synchronized with each other such that when the number of the anvils 16 disposed on the rotor 15 is N (N is equal to or greater than 1), the drive rotor 54 rotates N times per rotation of the rotor 15. In the present embodiment, N is 6.

As the rotor 15 is driven to rotate with a constant angular velocity in the counterclockwise direction and the drive rotor 54 is also driven to rotate with a constant angular velocity in the counterclockwise direction, as shown in FIGS. 1 and 3, the support 41 is driven to oscillate about the pivot O2 by crank motion of the reciprocating driving means 50. At this time, the sealing abutment surface 48a of the ultrasonic horn 48 reciprocates along the peripheral surface of the rotor 15.

As shown in FIG. 3, the second holding member 46 reciprocates such that its center Oa, which bisects the sealing abutment surface 48a of the ultrasonic horn 48 in a direction of movement, moves from the vertical reference line Oy over an angular range of +θ in the counterclockwise direction and over an angular range of −θ in the clockwise direction. The oscillating angle θ may be adjusted by changing radius R from the rotation center of the drive rotor 54 to the center of the connecting shaft 55 (see FIG. 1). Changing the radius R may also lead to adjustment of the relative velocity between the sealing abutment surface 16a of the anvil 16 and the sealing abutment surface 48a of the ultrasonic horn 48.

Furthermore, there is provided phase adjusting means for adjusting a rotational phase of the drive rotor 54. For instance, this may be achieved by changing the fixing position of the drive rotor 54 against the shaft 53 in a direction of rotation. When the drive rotor 54 is driven to rotate with a constant angular velocity, the velocity of the center Oa varies nearly following a trigonometric function curve; with the phase adjusting means, the position whereupon the velocity of the center Oa becomes maximum, may coincide with the vertical reference line Oy or may be shifted backward or forward from that position.

As shown in FIG. 1, a lead-in roll 61 is provided on a lead-in side of the rotor 15 and a lead-out roll 62 is provided on a lead-out side of the rotor 15, wherein a soft workpiece W extending in a band shape is passed over the lead-in roll 61, wound about the peripheral surface of the rotor 15 at a predetermined winding angle, and then let out from the lead-out roll 62.

Next, a sealing method using the sealing apparatus will be described.

The soft workpiece W shown in FIG. 6B is supplied in a direction indicated by an arrow (MD) to advance from the lead-in roll 61, through the peripheral surface 15a of the rotor 15, to the lead-out roll 62, as described above. The soft workpiece W is a partly-finished product in a process of manufacturing a shorts-type disposable diaper, wherein after seals Sa, Sb are formed in the soft workpiece W with the sealing apparatus 1, discrete disposable diapers may be obtained by cutting at positions between adjacent seals Sa, Sb.

Downstream of the lead-out roll 62, there is provided a pair of transport rolls, which rotate with a constant velocity to transport the soft workpiece W in MD with a constant velocity. The transport rolls are driven to rotate in synchronization with the rotor 15 so that the transportation velocity of the soft workpiece W may be synchronized with a peripheral velocity V0 with which the sealing abutment surfaces 16a of the anvils 16 are circulating.

FIG. 6A shows an unfolded state of the soft workpiece W prior to the state of FIG. 6B. Hereinafter, the soft workpiece W in the state of FIG. 6A is referred to as band 70. The band 70 has a first sheet 72, most part of which is hidden behind a second sheet 71 laid thereon. The first sheet 72 is of a larger width than the second sheet 71, so that on one side 70A, the first sheet 72 is folded back with a side edge 72a laid on the second sheet 71. On the other side 70B, likewise, the first sheet 72 is folded back with a side edge 72b laid on the second sheet 71.

On the one side 70A of the band 70, waist bands 75 are disposed between the first sheet 72 and the second sheet 71; on the other side 70B, waist bands 76 are disposed between the first sheet 72 and the second sheet 71. Also between the first sheet 72 and the second sheet 71, there are disposed leg bands 77, 78. The individual leg bands 77, 78 extend in a feed direction of the band 70 while undulating. In regions surrounded by the leg bands 77, 78, furthermore, there are formed leg holes 74, which will be openings for insertion of legs in a shorts-type disposable diaper.

The first sheet 72 and the second sheet 71 are breathable, liquid-impermeable and fusion-bondable by heat. For example, they may be a spunbonded or meltblown nonwoven fabric formed of thermoplastic synthetic fibers or a laminate thereof. Alternatively, one of the first sheet 72 and the second sheet 71 may be the above-mentioned nonwoven fabric, and the other a breathable thermoplastic plastic film.

Between adjacent leg holes 74, liquid absorbent bodies 73 are disposed on the second sheet 71. These liquid absorbent bodies 73, which may be of an hourglass or rectangular shape, are arranged at regular intervals in the feed direction of the band 70. The liquid absorbent body 73 may comprise ground pulp, a mixture of ground pulp and super absorbent polymer (SAP), a stack of hydrophilic nonwoven fabrics, air-laid pulp or the like. Such an absorbent material is wrapped up in a liquid-permeable topsheet. The individual liquid absorbent bodies 73 are bonded to the surface of the second sheet 71 through a hot-melt type adhesive or the like.

The topsheet may be a spunlaced nonwoven fabric, a through-air bonded nonwoven fabric, or a plastic film formed with liquid passage holes.

Along its longitudinally extending centerline Ow—Ow, the band 70 shown in FIG. 6A is folded into two with the liquid absorbent bodies 73 being directed inward, providing the soft workpiece W shown in FIG. 6B.

The circumferential pitch of the anvils 16 arranged on the peripheral surface 15a of the rotor 15 of the sealing apparatus 1 is identical to the pitch of the liquid absorbent bodies 73 arranged in MD of the soft workpiece W. It should be noted that between adjacent liquid absorbent bodies 73, the soft workpiece W has liquid absorbent body 73-free portions, whose dimension Lw in MD is larger than the circumferential dimension L1 of the anvil 16.

Accordingly, when the soft workpiece W is supplied to the periphery of the rotor 15, the liquid absorbent body 73 may be laid on the peripheral surface 15a of the rotor 15 at a position between adjacent anvils 16, and the liquid absorbent body 73-free portion, in which the first sheet 72, the second sheet 71, the waist bands 75, 76 and the leg bands 77, 78 are in a folded state, be laid on the sealing abutment surface 16a of the anvil 16, as shown in FIG. 4.

As shown in FIG. 4, the distance H at which the sealing abutment surface 16a of the anvil 16 is away from the peripheral surface 15a of the rotor 15 is set equal to or larger than a thickness Tw1 of liquid absorbent body 73-containing portions of the soft workpiece W. Therefore, the liquid absorbent body 73-containing portions may not project or may project only slightly beyond an orbital trajectory along which the sealing abutment surfaces 16a of the anvils 16 moves.

As the rotor 15 rotates and the second holding member 46 reciprocates, the liquid absorbent body 73-free portion of the soft workpiece W may be held between the sealing abutment surface 16a of the anvil 16 and the sealing abutment surface 48a of the ultrasonic horn 48; at this time, the clearance 6 between the sealing abutment surface 16a and the sealing abutment surface 48a may be finely adjusted in accordance with a thickness Tw2 of the liquid absorbent body 73-free portion of the soft workpiece W. Such fine adjustment may be performed by changing the height positions of the stoppers 21, 22. Alternatively, it may be performed by changing the fixing position of the second holding member 46 against the bracket 45. By such fine adjustment, the clearance δ between the sealing abutment surface 16a and the sealing abutment surface 48a may be set smaller than the thickness Tw2.

In a stopped state of the sealing apparatus 1 prior to the beginning of the sealing operation, the fluid pressure inside the fluid cylinders 23, 25 may be reduced to let the front bearing holder 7 and the rear bearing holder 9 descend away from the stopper 21 and the stopper 22, respectively. This results in a descent of the rotary shaft 11 along the vertical reference line Oy, increasing the clearance between the peripheral surface 15a of the rotor 15 and the sealing abutment surface 48a of the ultrasonic horn 48. In FIG. 3, the descent distance of the rotary shaft 11 is indicated by h.

After the soft workpiece W is wound about the peripheral surface 15a of the rotor 15, as shown in FIG. 1, the fluid pressure inside the fluid cylinders 23, 25 may be intensified to press the front bearing holder 7 and the rear bearing holder 9 against the stopper 21 and the stopper 22, respectively, thereby positioning the rotary shaft 11.

During the sealing operation, the rotor 15 is driven to rotate with a constant angular velocity in the counterclockwise (CCW) direction so that the sealing abutment surfaces 16a of the anvils 16 may continue to circulate with a constant peripheral velocity V0. The drive rotor 54 is also driven to rotate with a constant angular velocity in the counterclockwise (CCW) direction, wherein the rotary motion is transmitted to the support 41 through the connecting rod 51 so that the support 41 may reciprocate about the pivot O2.

The sealing abutment surface 48a of the ultrasonic horn 48 can reciprocate along a part of the orbital trajectory while keeping the clearance δ between it and the sealing abutment surface 16a of the anvil 16. At this time, the center Oa of the sealing abutment surface 48a of the ultrasonic horn 48 has a peripheral velocity Vt which varies following a trigonometric function, wherein the peripheral velocity Vt is almost (A·sinφ). φ may be a constant determined by the rotation angle of the drive rotor 54, and A be a constant determined by the turning radius R of the shaft 55. That is, the peripheral velocity Vt is a variable velocity which varies with time. The velocity of the sealing abutment surface 48a of the ultrasonic horn 48 at the center Oa is +Vt when moving in the direction of rotation of the rotor 15 and –Vt when moving in the opposite direction.

During a part of the term when the ultrasonic horn 48 moves in the counterclockwise direction, the soft workpiece W is held between the sealing abutment surface 48a of the ultrasonic horn 48 and either of the seal patterns 17a, 17b formed on the sealing abutment surface 16a of the anvil 16, thereby performing the sealing operation.

FIG. 4 illustrates the moment when the soft workpiece W is being held between the sealing abutment surface 16a and the sealing abutment surface 48a while the ultrasonic horn 48 is moving in the counterclockwise direction. At this time, the relative velocity of the sealing abutment surface 16a, as well as the soft workpiece W moving together, against the sealing abutment surface 48a of the ultrasonic horn 48 may be expressed by V0–Vt. The sealing operation may be performed with the soft workpiece W and the sealing abutment surface 48a of the ultrasonic horn 48 coming into sliding contact with each other with the relative velocity V0–Vt.

Thus, the seal patterns 17a, 17b, which are formed in pair on the sealing abutment surface 16a of the anvil 16 as shown in FIGS. 4 and 5, can be transferred to the soft workpiece W to provide the seals Sa, Sb, respectively.

The reciprocating driving means 50 has the rotational phase adjusting means for adjusting the rotational phase of the drive rotor 54. By adjusting the rotational phase with the rotational phase adjusting means, the position whereupon the velocity +Vt of the ultrasonic horn 48 becomes maximum may be set arbitrarily based on the seal patterns.

In the present embodiment, the seal patterns 17a, 17b, which are circumferentially separate from each other, are disposed on the sealing abutment surface 16a of the anvil 16 in symmetric relation about the centerline O3. Accordingly, the setting is such that the peripheral velocity +Vt becomes maximum when the center Oa of the sealing abutment surface 48a of the ultrasonic horn 48 is positioned midway between the seal patterns 17a, 17b. More preferably, the rotational phase of the drive rotor 54 is set such that the moment the center Oa coincides with the centerline O3 (or coincides with the vertical reference line Oy), the peripheral velocity +Vt becomes maximum.

When thus set, the center Oa of the sealing abutment surface 48a coincides with the seal pattern 17a immediately before the center Oa arrives at the vertical reference line Oy, as shown in FIG. 4, so that the soft workpiece W is held between the seal pattern 17a and the ultrasonic horn 48, forming the seal Sa. Subsequently, the center Oa of the sealing abutment surface 48a coincides with the seal pattern 17b immediately after the center Oa passes the vertical reference line Oy in the counterclockwise direction, so that the soft workpiece W is held between the seal pattern 17b and the ultrasonic horn 48, forming the seal Sb.

Here, if the setting is such that the peripheral velocity +Vt becomes maximum when the center Oa is positioned midway between the seal patterns 17a, 17b, the difference in relative velocity V0–Vt between the moment when the center Oa faces the seal pattern 17a and the moment when the center Oa faces the seal pattern 17b becomes extremely small. Preferably, the setting is such that the peripheral velocity +Vt becomes maximum when the center Oa coincides with the vertical reference line Oy, which results in that the center Oa faces the seal patterns 17a, 17b at an equal relative velocity V0–Vt.

In this case, it is preferred that the peripheral velocity +Vt coincides with the peripheral velocity V0 of the sealing abutment surface 16a when the center Oa of the sealing abutment surface 48a coincides with the vertical reference line Oy. More preferably, the peripheral velocity +Vt is slightly higher than the peripheral velocity V0 of the sealing abutment surface 16a when the center Oa of the sealing abutment surface 48a coincides with the vertical reference line Oy, which may reduce the relative velocity V0–Vt to zero at both the moment when the center Oa faces the seal pattern 17a and the moment when the center Oa faces the seal pattern 17b.

If the clearance δ between the sealing abutment surfaces 16a, 48a is made sufficiently smaller than the thickness Tw2 of the seal-forming portion of the soft workpiece W, the holding pressure to be applied to the soft workpiece W between the sealing abutment surfaces 16a, 48a may be set by the fluid pressure inside the fluid cylinders 23, 25. In this case, the soft workpiece W may always be held with a stable holding pressure between the sealing abutment surfaces 16a, 48a by setting the fluid pressure inside the fluid cylinders 23, 25 through the pressure setting means 30, certainly keeping the quality of the seals Sa, Sb constant.

In the sealing apparatus 1, since the relative velocity V0–Vt between the sealing abutment surfaces 16a, 48a during holding the soft workpiece W is sufficiently reduced (e.g., to zero), the application of sealing energy from the sealing abutment surfaces 16a, 48a to the soft workpiece W may be sufficiently prolonged. However, if the rotational velocity of the rotor 15, as well as the rotational velocity of the drive rotor 54, is significantly increased, the sealing energy from the ultrasonic horn 48 will not be properly applied to the soft workpiece W after all.

In the sealing apparatus 1, therefore, the change in the rotational velocity of the rotor 15 may be detected by the controller 33, adjusting the adjusting valve 32 in accordance with the rotational velocity and varying the fluid pressure inside the fluid cylinders 23, 25. Alternatively, the adjusting valve 32 may be manipulated by an operator in accordance with the rotational velocity. If the rotational velocities of the rotor 15 and drive rotor 54 are increased, therefore, the holding pressure to be applied to the soft workpiece W between the sealing abutment surfaces 16a, 48a may also be increased; conversely, if the rotational velocities are decreased, the holding pressure may be decreased, whereby the holding pressure may be set properly in accordance with the change in the application time of the sealing energy applied from the ultrasonic horn 48 to the soft workpiece W.

In the sealing apparatus 1, furthermore, the temperature of the anvil 16 is controlled to be always optimum with the cartridge heater and the temperature sensor housed in the anvil 16. This prevents the temperature of the anvil 16 during the sealing operation from being extremely lowered so that heat for sealing escapes to the anvil 16 to cause seal failure or from being extremely raised so that molten thermoplastic resin easily adheres to the seal patterns 17*a*, 17*b*.

In the sealing apparatus 1, as shown in FIG. 4, when the ultrasonic horn 48 moves in the counterclockwise direction, the soft workpiece W is first held between the seal pattern 17*a* that is positioned forward in the direction of rotation and the sealing abutment surface 48*a* of the ultrasonic horn 48, wherein the sealing operation is performed to form the seal Sa with the sealing abutment surface 48*a* in sliding contact with the soft workpiece W. Subsequently, the soft workpiece W is held between the next seal patter 17*b* and the sealing abutment surface 48*a*, wherein the seal Sb is formed with the sealing abutment surface 48*a* in sliding contact with the soft workpiece W. After that, the sealing abutment surface 48*a* of the ultrasonic horn 48 moves in the clockwise direction with a velocity −Vt. More specifically, the sealing abutment surface 48*a* moves back away from the anvil 16 in the clockwise direction to slide on the soft workpiece W in the region having no anvil 16. When the sealing abutment surface 48*a* moves again in the counterclockwise direction, then, the sealing operation shown in FIG. 4 is repeated with the ultrasonic horn 48 and the next one of the circulating anvils 16.

Accordingly, the sealing operation can be performed only when the soft workpiece W is being held between the seal patterns 17*a*, 17*b* and the ultrasonic horn 48, even if the ultrasonic vibration is continuously applied to the ultrasonic horn 48. However, it is also possible to detect the rotational phase of the rotor 15 and to control such that the ultrasonic vibration may be applied to the ultrasonic horn 48 only when the soft workpiece W is being held between the seal patterns 17*a*, 17*b* and the ultrasonic horn 48.

The sealing apparatus may also be provided with detection means such as optical sensor for detecting the thickness of the soft workpiece W before and after the vertical reference line Oy, whereby when a transport problem occurs to let the liquid absorbent body 73 of the soft workpiece 73 run on to the sealing abutment surface 16*a* of the anvil 16, the adjusting valve 32 may be operated immediately to reduce the fluid pressure inside the fluid cylinders 25, 25 for descent of the rotary shaft 11, which immediately prevent occurrence of jam of the soft workpiece W.

After the sealing operation is thus performed to provide the seals Sa, Sb in the soft workpiece W, as shown in FIG. 6B, then, the soft workpiece W may be separated into individual shorts-type disposable diapers by using a cutter provided downstream of the sealing apparatus 1, wherein cutting may be performed along cut lines C1 which are positioned between adjacent seals Sa, Sb.

Although the present invention has been illustrated and described with respect to exemplary embodiment thereof, it should be understood by those skilled in the art that the foregoing and various other changes, omission and additions may be made therein and thereto, without departing from the spirit and scope of the present invention.

For example, the first holding member on the rotor 15 may be an ultrasonic horn and the second holding member on the support 41 be an anvil. Furthermore, the first holding member and the second holding member should not be limited to such an ultrasonic horn and an anvil, but may be any devices, such as heat-sealing heads, as long as they can apply a sealing energy to a workpiece. It is also possible to adopt a rotating cam as the reciprocating driving means 50 and to control the motion of the connecting rod 51 by the rotating cam.

It should be also noted that a stack of sheets, such as nonwoven fabrics, films or a combination thereof, may be sealed with the sealing apparatus 1 prior to and separately from a process of manufacturing a disposable diaper, a sanitary napkin or the like, so that the composite material can be supplied to the manufacturing process after sealing.

According to the present invention, as has been described hereinabove, sealing operation, in which the soft workpiece is transported by the continuously rotating rotor, may be performed with a relative velocity of the first holding member and the workpiece against the second holding member being kept low. Therefore, application of sealing energy to the workpiece may be sufficiently prolonged, enabling high speed sealing operation with the rotor being driven to rotate with a high velocity.

The present invention should not be understood as limited to the specific embodiment set out above but to include all possible embodiments which can be embodied within a scope encompassed and equivalent thereof with respect to the feature set out in the appended claims.

What is claimed is:

1. A sealing apparatus, comprising:
   a first holding member having a first sealing abutment surface; and
   a second holding member having a second sealing abutment surface;
   said first and second holding members being adapted to hold a flexible workpiece between the first and the second sealing abutment surfaces for sealing;
   the first holding member being disposed on a periphery of a rotor with the first sealing abutment surface directed radially outward, the second holding member being supported by a support with the second sealing abutment surface directed to face the first sealing abutment surface;
   wherein the apparatus further comprises
   rotational driving means for driving the rotor to rotate; and
   reciprocating driving means for driving the support and moving the second sealing abutment surface in reciprocating motion along a part of an oibital trajectory of the first sealing abutment surface, thereby enabling holding of the workpiece between the first and the second sealing abutment surfaces for sealing when the second holding member moves in the same direction as the first holding member.

2. The sealing apparatus according to claim 1, comprising N said first holding members disposed on the rotor, where N is greater than 1;
   wherein said reciprocating driving means is further for performing the reciprocating motion of the second holding member N cycles per revolution of the rotor.

3. The sealing apparatus according to claim 1, wherein
   said rotational driving means is further for moving the first sealing abutment surface at a constant peripheral velocity and for driving the rotor to rotate with a constant angular velocity,
   said reciprocating driving means is further for moving the second sealing abutment surface with a varying peripheral velocity, so that the first and the second sealing abutment surfaces, while holding the workpiece therebetween for sealing, move with a varying relative velocity.

4. The sealing apparatus according to claim 3, further comprising
    two seal patterns separate from each other in a circumferential direction of the rotor and disposed on the first sealing abutment surface of the first holding member; and
    phase adjusting means for adjusting a phase of the peripheral velocity of the second sealing abutment surface such that the relative velocity of said first and second sealing abutment surfaces is at a minimum when a center of the second holding member is positioned midway between the two seal patterns.

5. The sealing apparatus according to claim 1, wherein
    the support is rotatable in reciprocating motion about a pivot substantially coinciding with or almost coinciding with a rotation center of the rotor; and
    the reciprocating driving means comprises a crank mechanism for converting a uniform rotaly motion into the reciprocating motion of the support.

6. The sealing apparatus according to claim 1, further comprising
    a rotary shaft of the rotor, wherein said rotary shaft is movable toward the second holding member; and
    pressure setting means for setting a holding pressure to be applied to the workpiece between the first and the second sealing abutment surfaces with the rotor being pressed against the second holding member.

7. The sealing apparatus according to claim 6, wherein said pressure setting means is further for adjusting the holding pressure in accordance with a rotational velocity of the rotor.

8. A sealing methods, comprising:
    feeding a workpiece between a first holding member having a first sealing abutment surface and a second holding member having a second sealing abutment surface for sealing;
    driving the first holding member to circulate with the first sealing abutment surface directed outward in a direction normal to an orbital trajectory thereof, wherein the workpiece is fed onto the first holding member so as to move along with the first sealing abutment surface;
    reciprocating the second holding member along a part of the orbital trajectory with the second sealing abutment surface directed to face the first sealing abutment surface; and
    sealing portions of the workpiece together when said portions are held in a nip between said first and second sealing abutment surfaces moving in the same direction.

9. The sealing method according to claim 8, further comprising providing a crank mechanism for converting a uniform rotary motion into a reciprocating motion;
    wherein said reciprocating comprises driving the second holding member with said crank mechanism.

10. The sealing method according to claim 8, further comprising providing N said first holding members spaced at a constant pitch, where N is greater than 1;
    wherein said reciprocating comprises performing the reciprocating motion of the second holding member N cycles per revolution of each first holding member.

11. The sealing method according to claim 8, wherein
    the workpiece comprises liquid absorbent bodies arranged at an interval in a feed direction of said feeding and fusion-bondable sheets supporting the liquid absorbent bodies; and
    said sealing comprises sealing the sheets at positions between adjacent said liquid absorbent bodies.

12. The sealing method according to claim 8, wherein
    said driving comprises moving the first sealing abutment surface at a constant peripheral velocity; and
    said reciprocating comprises moving the second sealing abutment surface in reciprocating motion at a varying peripheral velocity so that, when said portions of the workpiece are held in said nip, the first and the second sealing abutment surfaces have a varying relative velocity.

13. The sealing method according to claim 8, wherein said reciprocating comprises moving the second holding member in reciprocating motion about a pivot substantially coinciding with a rotation center of the first holding member in said driving.

14. The sealing method according to claim 8, further comprising moving a rotary shaft, about which the first holding member circulates during said driving, toward or away from the second holding member to adjust a holding pressure in said nip.

15. The sealing method according to claim 14, wherein the holding pressure is adjusted in accordance with a rotational velocity of the first holding member.

16. The sealing method according to claim 12, further comprising
    providing two seal patterns on the first holding member and separate from each other in a circulating direction of the first holding member; and
    adjusting the peripheral velocity of the second sealing abutment surface in phase such that the relative velocity is at a minimum when a center of the second holding member is positioned midway between the two seal patterns.

17. The sealing apparatus according to claim 1, wherein said reciprocating driving means is further for reciprocating the second sealing abutment surface on an arc and wherein said second sealing abutment surface is kept at a constant distant from a center of said arc at all times.

18. A sealing apparatus, comprising:
    at least one first holding member having a first sealing abutment surface;
    a second holding member having a second sealing abutment surface;
    said first and second holding members being adapted to hold a flexible workpiece between the first and the second sealing abutment surfaces for sealing;
    the first holding member being disposed on a periphery of a rotor with the first sealing abutment surface directed radially outward, the second holding member being supported by a support with the second sealing abutment surface directed to face the first sealing abutment surface;
    said rotor being rotatable about a rotary shaft; and
    a reciprocating driving element adapted to drive the support and move the second sealing abutment surface in reciprocating motion along a part of an orbital trajectory of the first sealing abutment surface, thereby enabling holding of the workpiece between the first and the second sealing abutment surfaces for sealing when the second holding member moves in the same direction as the first holding member.

19. The sealing apparatus according to claim 18, wherein said second holding member being rotatable in the reciprocating motion about a rotational axis extending through said rotor.

20. The sealing apparatus according to claim 18, wherein said second holding member being rotatable in the reciprocating motion about a pivot, and said second holding member is limited to rotate less than 360° about said pivot.

* * * * *